United States Patent [19]

Houghton et al.

[11] Patent Number: 5,371,081
[45] Date of Patent: Dec. 6, 1994

[54] N-SUBSTITUTED PHENOXAZINES FOR TREATING MULTIDRUG RESISTANT CANCER CELLS

[75] Inventors: Peter J. Houghton, Memphis, Tenn.; Julie K. Horton, Germantown, Md.; Kuntebommanahalli N. Thimmaiah, Karnataka, India

[73] Assignee: St. Jude Children's Research Hospital, Memphis, Tenn.

[21] Appl. No.: 126,812

[22] Filed: Sep. 24, 1993

Related U.S. Application Data

[63] Continuation of Ser. No. 744,619, Aug. 12, 1991, abandoned.

[51] Int. Cl.⁵ ............... A61K 31/535; C07D 265/38; C07D 413/06
[52] U.S. Cl. .................... 514/229.8; 514/9; 514/10; 544/73; 544/102
[58] Field of Search ............ 544/73, 102; 514/9, 514/10, 229.8

[56] References Cited

U.S. PATENT DOCUMENTS

| | | | |
|---|---|---|---|
| 4,562,176 | 12/1985 | Sengupta | 514/17 |
| 4,590,277 | 5/1986 | Atwell et al. | 546/105 |
| 4,680,382 | 7/1987 | Sengupta | 530/317 |

FOREIGN PATENT DOCUMENTS

| | | | |
|---|---|---|---|
| 569697 | 7/1958 | Belgium | 544/102 |
| 738992 | 7/1966 | Canada | 544/102 |
| 1178203 | 11/1984 | Canada | |
| 56-166115 | 12/1981 | Japan | |
| 56-166116 | 12/1981 | Japan | |
| 61-130217 | 6/1986 | Japan | |
| 850334 | 10/1960 | United Kingdom | |

OTHER PUBLICATIONS

*Drug Evaluations*, 6th ed., (1986), American Medical Assn., pp. 1081, 1171-1179, 1200-1201, 1204, 1207, 1218.

The Merck Index, 11th ed., (1989), Merck & Co., Inc., p. 445.

Thimmaiah et al., CA115:197724m (1990).
Suzuki et al, CA 83:193345m (1975).
Gal et al, CA 60:1738e-g (1963).
Samolovova et al, CA 55:23540i (1961).

(List continued on next page.)

*Primary Examiner*—Mukund J. Shah
*Assistant Examiner*—Philip I. Datlow
*Attorney, Agent, or Firm*—Scully, Scott, Murphy & Presser

[57] ABSTRACT

Disclosed are compounds useful in potentiating the cytotoxic effect of chemotherapeutic agents, the compounds having the formula:

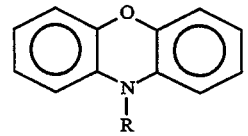

and pharmacologically acceptable salts thereof, wherein R is —H or —[C(O)]$_a$—(CH$_2$)$_b$—A, a is 0-1 and b is 0-6 provided that a and b are not both zero; and A is selected from the group consisting of —NR$_1$R$_2$ wherein R$_1$ and R$_2$ are independently alkyl having 1 to 4 carbon atoms, and either or both of R$_1$ and R$_2$ are optionally substituted with —OH;

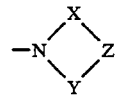

wherein X and Y are independently alkylene having 1 to 4 carbon atoms, and Z is —O—, —N(R$_3$)—, or —CH(R$_4$)—, wherein R$_3$ and R$_4$ are each hydrogen or alkyl having 1 to 4 carbon atoms optionally substituted with a hydroxyl group; halide; and trihalomethyl.

62 Claims, No Drawings

OTHER PUBLICATIONS

Sen et al, CA 56:8711b (1961).
Antoni, CA 60:8023a (1963).
Caldwell, CA 53:17155c (1959).
Frangatos et al, CA 54:21103c (1960).
Shirley et al., CA 57:8567d (1961).
Vanderhaeghe et al, CA 56:10137g (1961).
Yarmukhametova et al, CA 84:4884y (1975) and CA 92:64849 (1979).
Ford et al., "Structural Features Determining Activity of Phenothiazines and Related Drugs for Inhibition of Cell Growth and Reversal of Multidrug Resistance", *Molecular Pharmacology*, 35:105–115 (1988).
Aklyama et al., "Circumvention of Multiple–Drug Resistance in Human Cancer Cells by Thioridazine, Trifluoperazine, and Chlorpromazine", *JNCL*, vol. 76, No. 5, May 1986, pp. 839–844.
Tsuruo et al., "Increased Accumulation of Vincristine and Adriamycin in Drug–risistance P388 Tumor Cells Following Incubation with Calcium Antagonists and Calmodulin Inhibitors", *Cancer Research*, 42, pp. 4730–4733, Nov. 1982.
Zamora et al., "Physical–Chemical Properties Shared by Compunds that Modulate Multidrug Resistance in Human Leukemic Cells", *Molecular Pharmacology*, 33:454–462 (1988).
Kessel et al., "Promotion of Daunorubicin Uptake and Toxicity by the Calcium Antagonist Tiapamil and Its Analogs", *Cancer Treatment Reports*, vol. 69, No. 6, Jun. 1985, pp. 673–676.
Shiraishi et al., "Lysosomotropic Agents Reverse Multiple Drug Resistance in Human Cancer Cells", *Cancer Letters*, 30 (1986) pp. 251–259.
Yamaguchi et al., "Overcoming Drug Resistance in Cancer Cells with Synthetic Isoprenoids", *JNCL*, vol. 76, No. 5, May 1986, pp. 947–953.
Sloviter, "Halogenated Benzophenoxazine Dyes", [Contribution from the Harrison Department of Surgical Research, School of Medicine, University of Pennsylvania, and the Department of Neurosurgery, Hospital of the University of Pennsylvania], vol. 71, pp. 3360–3362, J. Amer. Chem. Soc. (1949).
Crossley et al., "Chemotherapeutic Dyes. I. 5–Aralkylamino–9–alkylaminobenzo[a]phenoxazines", *Journal of the American Chemical Society*, vol. 74, Feb. 5, 1952, No. 3, pp. 573–586.
Sen et al., "Potential Carcinostatic Derivatives of Benzo[a]– and Benzo[b]phenoxazine", [Contribution from the Department of Chemistry, the University of Tennessee], Oct. 1961, pp. 3861–3863, J. Org. Chem.
Sen et al., "Syntheses of 5–[4–{N,N–Bis(2–chloroethyl)amino}benzylamino]–9–N,N–dialkyl–aminobenzo[a]–phenoxazonium Chlorides", *Indian Journal of Chemistry*, vol. 21B, Jul. 1982, pp. 642–645.
Cincotta et al., "Novel Red Absorbing Benzo[a]–phenoxazinium and Benzo[s]phenothiazinium Photosensitizers: In Vitro Evaluation", *Photochemistry and Photobiology*, vol. 46, No. 5, pp. 751–758, 1987.
Jain et al., "Potential Anticancer Agents: Synthesis of Amides & Esters of 2–Amino–4,6–dimethyl–3–oxo–phenoxazine–I,9–dicarboxylic Acid", *Indian Journal of Chemistry*, vol. 15B, Feb. 1977, pp. 163–164.
Palmer et al., "Potential Antitumor Agents. 54. Chromophore Requirements for In Vivo Antitumor Activity Among the General Class of Linear Tricyclic Carboxamides", *J. Med. Chem.*, 1988, 31, pp. 707–712.
Sengupta et al., "'Reverse' and 'Symmetrical' Analogues of Actinomycin D: Metabolic Activation and In Vitro and In Vivo Tumor Growth Inhibitory Activities", *J. Med. Chem.*, 1985, vol. 28, No. 5, pp. 620–628.
Kanzawa, et al., "Antitumor Activity of Haloacetylcarbazole Derivatives", *Gann, The Japanese Journal of Cancer Research*, 64, pp. 391–396 (1973).

N-SUBSTITUTED PHENOXAZINES FOR TREATING MULTIDRUG RESISTANT CANCER CELLS

This invention was made with Government support under Contract No. CA-23099 awarded by the National Institutes of Health. The Government has certain rights in the invention.

This is a continuation of copending application(s) Ser. No. 744,619 filed on Aug. 12, 1991, now abandoned.

BACKGROUND OF THE INVENTION

The present invention is directed to chemo-therapy of cancer.

A major reason for failure of treatment of cancer patients is resistance to conventional chemo-therapeutic agents. One type of drug resistance, called multi-drug resistance (MDR) is characterized by cross-resistance to functionally and structurally unrelated chemotherapy drugs, such as doxorubicin, vincristine (VCR), vinblastine (VLB), colchicine, and actinomycin D. A number of drugs appear to be active in modifying MDR in model systems, including the calcium channel blocker, verapamil (VRP), the calmodulin inhibitor, trifluoperazine, the anti-arrhythmic drug, quinidine, reserpine, cyclosporin A, Vinca alkaloid analogs, dihydropyridines, and pyridine analogs. Thus, it can be seen that agents that reverse MDR apparently do not seem to have common features. Although several of these MDR-reversing agents have been or are now being tested clinically in cancer patients, they have largely failed to enhance sensitivity to the chemotherapeutic agent. Instead, serious toxicities develop at or below plasma drug levels required for MDR reversal in vitro.

A tricyclic compound, phenoxazine, has been found to potentiate the uptake of VCR and VLB in MDR GC3/Cl and KBCh®-8-5 cells to a greater extent than verapamil. While this discovery has utility and holds promise, it would be desirable to identify derivatives of phenoxazine which would modulate MDR and which show even higher stability and lower toxicity.

BRIEF SUMMARY OF THE INVENTION

In one aspect, the present invention comprises compounds of formula (1):

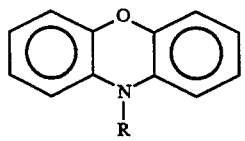

(1)

and pharmacologically acceptable salts thereof,
wherein R is $-[C(O)]_a-(CH_2)_b-A$;
wherein a is 0 or 1 and b is an integer from 0 to 6, provided that a and b are not both zero;
A is selected from the group consisting of $-NR_1R_2$ wherein $R_1$ and $R_2$ are independently alkyl having 1 to 4 carbon atoms, and either or both of $R_1$ and $R_2$ are optionally substituted with $-OH$;

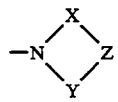

wherein X and Y are independently alkylene having 1 to 4 carbon atoms, and Z is $-O-$, $-N(R_3)-$ or $-CH(R_4)-$, wherein $R_3$ is hydrogen or alkyl having 1 to 4 carbon atoms optionally substituted with a hydroxyl group, and wherein $R_4$ is hydrogen or alkyl having 1 to 4 carbon atoms optionally substituted with a hydroxyl groups;
halide; and trihalomethyl.

Other aspects of the invention include combinations of one or more compounds of formula (1), wherein R is $-H$ or $-[C(O)]_a-(CH_2)_b-A$ and a, b, and A are as defined above, with one or more chemotherapeutic agents; the method of potentiating the effect of the chemotherapeutic agent by administering such a compound; and the method of killing or inactivating tumor cells by administering to the cell a chemotherapeutic agent and such a compound.

DETAILED DESCRIPTION OF THE INVENTION

As described in more detail below, the present invention provides novel and effective means for potentiating the desired cytotoxic effect of anticancer drugs in tumor cells and especially in multidrug-resistant (MDR) cells.

One preferred group of compounds of the formula (1) is the N-alkyl derivatives, in which a is 0 in formula (1). Of those compounds wherein a is 0, the more preferred include those in which b is 3 or 4, denoting unbranched propylene and butylene moieties; $R_1$ and $R_2$ each are ethyl, n-propyl, ω-hydroxyethyl, or ω-hydroxypropyl; X and Y are each $-CH_2-$ or $-CH_2CH_2-$ and, more preferably, both X and Y are $-CH_2CH_2-$; and $R_3$ and $R_4$ are each $-H$ or ethyl, propyl, e.g. n-propyl, ω-hydroxyethyl or ω-hydroxypropyl. Other more preferred embodiments when a is 0 are those derivatives wherein b is 3 or 4 and A is halogen, preferably chloro.

Another preferred group of compounds of formula (1) is the N-acyl derivatives, in which a is 1 in formula (1). Of those compounds wherein a is 1, the more preferred include those in which b is 1 or 2, more preferably 1; $R_1$ and $R_2$ are each ethyl, n-propyl, ω-hydroxyethyl or ω-hydroxypropyl; X and Y are each $-CH_2-$ or $-CH_2CH_2-$, and more preferably, both X and Y are $-CH_2CH_2-$; each of $R_3$ and $R_4$ is $-H$ or ethyl, n-propyl, ω-hydroxyethyl or ω-hydroxypropyl. Other more preferred embodiments are those in which b is 0 or 1 and A is trihalomethyl, preferably trichloromethyl or trifluoromethyl; and in which b is 1 or 2 and A is halogen, preferably chloro.

As used herein, unless specified otherwise, "alkyl" means saturated, branched or unbranched groups of the formula $-(C_nH_{2n+1})$; "halo" or "halogen" means fluoro, chloro, bromo, and/or iodo; and the optional hydroxyl and halo substituents disclosed herein can be on any carbon of an alkyl or alkylene group.

The compounds of this invention form salts, which are also within the scope of the invention, with various inorganic and organic acids. The pharmacologically acceptable acid addition salts of the compounds of the present invention may be prepared by conventional means, such as by reacting with an appropriate acid providing the desired anion, either in a solvent or medium in which the salt is insoluble, or in water. The salts of strong acids are preferred. As exemplary, but not limiting, of pharmacologically acceptable acid salts are the salts of hydrochloric, hydrobromic, sulfuric, nitric, acetic, fumaric, malic, maleic, tartaric and citric acids.

In general, the synthesis of the N-alkyl and N-acyl derivatives is straightforward. N-alkylation can be achieved in the presence of basic condensing agents like sodium amide. The general procedure for preparing the N-alkyl derivatives of formula (1) consists of the condensation of phenoxazine with the appropriate α, ω-dialkylhalide in such as Cl—$(CH_2)_b$—Br wherein b is 1 to 6, in the presence of sodium amide, either in liquid ammonia or in an anhydrous solvent such as toluene or benzene. For instance, the reaction of phenoxazine with mixed chlorobromoalkanes in the presence of sodium amide gives reactive N-chloroalkylphenoxazines, which can then be converted to the desired compound by reaction with an intermediate of the formula H—$(CH_2)_b$—A wherein b and A have the meanings set forth above.

More specifically, compounds such as those described in Examples 1-14 below can be prepared by first alkylating phenoxazine with 1-bromo-3-chloropropane or 1-bromo-4-chloropropane to produce 10-(3'-chloropropyl) phenoxazine or 10-(4'-chlorobutyl)phenoxazine, alkylation being accomplished by first converting phenoxazine to the anionic species using the strong base, sodium amide. Iodide-catalyzed nucleophilic substitution of the propyl or butyl chloride with various secondary amines (e.g. N,N-diethylamine, N,N-diethanolamine, morpholine, piperidine, pyrrolidine and β-hydroxyethyl-piperazine) by refluxing for about 20 hours with potassium carbonate in anhydrous acetonitrile affords the free bases of formula (1).

The acyl derivatives of formula (1) can be synthesized by acylating phenoxazine with a compound of the formula Cl—C(O)—$C(CH_2)_{0-6}$—Cl and then reacting the product with an amine of the formula H—A, wherein A has the meaning given above in anhydrous acetonitrile containing potassium iodide. The haloacetylphenoxazine can be prepared by reacting phenoxazine with the anhydride $(C(halo)_3CO)_2O$.

All the compounds described in Examples 1-14 were separated and purified by column chromatography or recrystallization and dried under high vacuum. The structures were established by UV-, IR, $^1H$— and $^{13}C$-NMR and EIMS spectral data, and by elemental analyses. The physical properties of the compounds are given in Table I. The UV-spectral data of N-substituted phenoxazines are in close agreement with the spectral characteristics of analogous heterocycles. The IR bands also indicate the presence of characteristic functional groups, and peaks at 1670–1695 cm$^{-1}$ indicated the presence of >C=O group in the acyl derivatives. The $^1H$-NMR in CDCl$_3$, typical of phenoxazine compound, showed eight aromatic protons and the data are in accordance with the structures assigned. The assignment of protons is fully supported by the integration curves. The $^{13}C$-NMR spectrum of each N-substituted phenoxazine exhibited size signals representing 12 aromatic carbons. The GC-Mass spectrum showed an intense molecular ion peak (M+) for each of the compounds characteristic of the phenoxazine type of structure. The spectral data are consistent with the assigned structures.

SYNTHESIS AND ANALYSIS

In the syntheses and experiments described below, melting points were recorded on a Perkin-Elmer Model 1320 spectrophotometer, as KBr pellets; UV-spectra were recorded in MeOH on a Perkin-Elmer Lambda 3B spectrophotometer. Elemental analyses were performed and found values within 0.4% of theoretical, unless otherwise noted. Reactions were monitored by tlc. For tlc, Analtech silica gel GF plates (20×20 cm, 250 microns, glass-backed), with petroleum ether-ethylacetate (9.7:0.3 by volume, system A), and ethylacetate-methanol (9.9:0.1 by volume, system B) as solvents were used. Column chromatography utilized silica gel Merc grade 60 (230–400 mesh, 60 Å). $^1H$- and $^{13}C$-NMR spectra were recorded in CDCl$_3$ solution in a 5 mm tube on an IBM NR 200 AF Fourier transform spectrometer with tetramethylsilane as internal standard. Chemical shifts are expressed as """ (ppm) values. The spectrometer was internally locked to the deuterium frequency of the solvent. Electron-impact mass spectra (EIMS) were recorded on a Ribermag R10-10C GC-mass spectrometer with an upper mass limit of 1500 AMU. All chemicals and supplies were obtained from standard commercial sources unless otherwise indicated. Phenoxazine, secondary amines indicated in the text, and anhydrous organic solvents were purchased from Aldrich Chemical Co. (Milwaukee, Wis.). Vincristine sulfate (oncovin) was purchased from Eli Lilly and Co. (Indianapolis, Ind.), and vinblastine sulfate was from Cetus Corporation (Emeryville, Calif.). [G-$^3$H]vincristine (sp. act (specific activity) 7.1 Ci/mmol) and [G-$^3$H]vinblastine (sp. act. 10.1 Ci/mmol) were obtained from Amersham Corporation (Arlington Heights, Ill.). Verapamil hydrochloride, colchicine, RPMI-1640 medium, powder with glutamine and without sodium bicarbonate were purchased from the Sigma Chemical Co. (St. Louis, Mo.).

The synthesis of representative compounds of formula (1) is described below. Each of the indicated compounds in these Examples is considered a preferred embodiment of the present invention.

EXAMPLE 1

10-(3'-chloropropyl)-phenoxazine. To a suspension of sodium amide (1.72 g) in 100 ml of liquid ammonia, 7 g (0.038 mol) of phenoxazine was added. After stirring for 30 minutes, 6.3 g (0.04 mol., 3.96 mL) of 1-bromo-3-chloropropane was added slowly with constant stirring. After one more hour, ammonia was allowed to evaporate and solid ice pieces were added carefully followed by cold water. When the reaction ceased, the mixture was extracted three times with ether. The ether solution was washed three times with water, dried over anhydrous sodium sulfate and evaporated. The residue was chromatographed on silica gel. Petroleum ether-ethylacetate (9 mL+3 mL) eluted the pure title compound (7.94 g) as white crystals. VU-$\lambda_{max}$ (MeOH) 218, 238 and 321 nm; IR (KBr) 3070, 2860, 1630, 1490, 1380, 1275, 920, 815 and 740 cm$^{-1}$; $^1H$-NMR (δ) 6.47–6.82 (m, 8H, ArH, $H_1$–$H_4$ and $H_6$–$H_9$), 2.11 (m, 2H, $H_1$), 3.63 (m, 2H, $H_K$), and 3.69 (m, 2H, $H_m$); $^{13}C$-NMR ($^1H$ decoupled) 111.23 ($C_1$ and $C_9$), 115.50 ($C_4$ and $C_6$), 121.07 ($C_3$ and $C_7$), 123.70 ($C_2$ and $C_8$), 133.03 ($C_{1'}$ and $C_{9'}$), 144.92 ($C_{4'}$ and $C_{6'}$), 27.82 ($C_1$), 41.09 ($C_K$) and 42.63 ($C_m$); EIMS (m/z) 259 (M+).

EXAMPLE 2

10-(3'-diethylaminopropyl)phenoxazine. 1 g (4.31 mmol) of the product of Example 1 was dissolved in 150 mL of anhydrous acetonitrile, and 1.5 g KI, 2.13 g K$_2$CO$_3$ and 1.6 mL (15.4 mmol) of N,N-diethylamine were added. The mixture was refluxed overnight until a substantial amount of product was formed (TLC, System B, $R_f$=0.40). The reaction mixture was diluted with water and extracted with ether three times. The ether layer was washed with water and dried over anhydrous $Na_2SO_4$ and evaporated. The crude oil was subjected to column chromatography for purification. Ethylacetate-petroleum ether (50 mL+50 mL) eluted the title compound as the free base as a colorless oil, which was dried and used for NMR studies. An ethereal solution of the free base was treated with an excess of tartaric acid to separate the hygroscopic tartrate salt (1.2 g). UV-$\lambda_{max}$ (MeOH) 215, 238 and 320 nm; IR (CHCl3) 3378, 2974, 2838, 1453, 1375, 1155, 973 and 722 cm$^{-1}$; $^1$H-NMR ('δ') 6.51-6.80 (m, 8H, ArH, $H_1$-$H_4$ and $H_6$-$H_9$), 1.16 (t, 6H, $H_c$ and $H_d$), 2.50 (q, 4H, $H_a$ and $H_b$, J=7 Hz), 3.42-3.63 (m, 4H, $H_k$ and $H_m$); $^{13}$C-NMR 111.54 ($C_1$ and $C_9$), 115.49 ($C_4$ and $C_6$), 121.21 ($C_3$ and $C_7$), 123.85 ($C_2$ and $C_8$), 132.72 ($C_{1'}$ and $C_{9'}$), 144.95 ($C_{4'}$ and $C_{6'}$), 8.21 ($C_c$ and $C_d$), 19.90 ($C_1$), 40.72 ($C_a$ and $C_b$), 45.87 ($C_m$), and 48.50 ($C_k$); EIMS (m/z) 296 (M+).

EXAMPLE 3

10-(3'-bishydroxyethylaminopropyl)phenoxazine.
The procedure used for Example 2 was-repeated with 1 g, (4.31 mmol) of the product of Example 1, 1.5 g KI, and 1.62 g (15.4 mmol, 1.5 mL) of diethanolamine. Recrystallization of the solid in ethylacetate and petroleum ether gave (1.14 g) of the title compound in the pure form. UV-$\lambda_{max}$ (MeOH) 218, 239, and 322 nm; IR (KBr) 3300, 2960, 2880, 1590, 1490, 1440, 1375, 1270, 1190, 1125, 1075, 1040, 890, 840, and 740 cm$^{-1}$; $^1$H-NMR ('δ') 6.44-6.78 (m, 8H, ArH, $H_1$-$H_4$ and $H_6$-$H_9$), 1.71-1.82 (m, 2H, $H_1$), 2.54-2.61 (t, 4H, $H_a$ and $H_b$, J=6 Hz), 3.39-3.68 (m, 8H, $H_k$, $H_c$, and $H_d$ and $H_m$), and 2.95 (s,$H_e$ and $H_f$, disappearing on $D_2O$ exchange); $^{13}$C-NMR 111.37 ($C_1$ and $C_9$), 115.33 ($C_4$ and $C_6$), 120.80 ($C_3$ and $C_7$), 123.66 ($C_2$ and $C_8$), 133.25 ($C_{1'}$ and $C_{9'}$), 144.99 ($C_{4'}$ and $C_{6'}$), 22.42 ($C_1$), 41.83 ($C_a$ and $C_b$), 52.38 ($C_m$), 55.91 ($C_k$) and 59.64 ($C_c$ and $C_d$); EIMS (m/z) 328 (M+).

EXAMPLE 4

10-(3'-N-morpholinopropyl)phenoxazine. The procedure used for Example 2 was repeated with 1 g of the product of Example 1, 1.5 g KI, 2.0 g $K_2CO_3$ and 1.4 g (15.40 mmol, 1.34 mL) of morpholine. The oily residue was purified by column chromatography to give the title compound as a brown oil. An ethereal solution of the free base was treated with ethereal hydrochloride to give the hydro-chloride salt (1.07 g). UV-$\lambda_{max}$ (MeOH) 216, 239, and 320 nm; IR (KBr) 3200, 1495, 1380, 1280, 1230, 1135, 1100, 1050, 1020, 980, 870, 830, 760 and 735 cm$^{-1}$; $^1$H-NMR ('δ') 6.63-6.81 (m, 8H, ArH, $H_1$-$H_4$ and $H_6$-$H_9$), 1.78 (m, 2H, $H_1$), 2.40 (t, 4H, $H_a$ and $H_b$, J=12 Hz), 3.45-3.80 (m, 8H, $K_k$, $H_m$, $H_c$ and $H_d$); $^{13}$C-NMR 111.64 ($C_1$ and $C_9$), 115.80 ($C_4$ and $C_6$), 121.59 ($C_3$ and $C_7$), 123.91 ($C_2$ and $C_8$), 133.50 ($C_{1'}$ and $C_{9'}$), 145.11 ($C_{4'}$ and $C_{6'}$), 20.06 ($C_1$), 40.93 ($C_a$ and $C_b$), 51.91 ($C_m$), 55.20 ($C_k$), and 63.50 ($C_c$ and $C_d$); EIMS (m/z) 310 (M+).

EXAMPLE 5

10-(3'-N-piperidinopropyl)phenoxazine. The procedure used for Example 2 was used with 1.12 g (4.31 mmol) of the product of Example 1, 1.5 g IH, 2.4 g $K_2CO_3$ and 1.5 g (17.62 mmol, 1.74 mL) of piperidine. The product was chromatographed on silica gel with petroleum ether-ethylacetate (1:1 by volume) to obtain the pure title compound in the form of an oil. By adding ethereal hydrochloride to the ether solution of the free base, the hydrochloride salt (1.15 g) was obtained. UV-$\lambda_{max}$ (MeOH) 218, 238 and 320 nm; IR (KBr) 3300, 2940, 2680, 1595, 1495, 1385, 1275, 1160, 1050, 825 and 745 cm$^{-1}$; $^1$H-NMR ('δ') 6.56-6.86 (m, 8H, ArH, $H_1$-$H_4$ and $H_6$-$H_9$), 1.53 (m, 6H, $H_c$, $H_d$ and $H_e$), 2.30 (m, 2H, $H_1$), 2.56-2.67 (m, 4H, $H_a$ and $H_b$), and 3.45-3.70 (m, 4H, $H_k$ and $H_m$); $^{13}$C-NMR 111.65 ($C_1$ and $C_9$), 115.62 ($C_4$ and $C_6$), 121.38 ($C_3$ and $C_7$), 123.88 ($C_2$ and $C_8$), 132.73 ($C_{1'}$ and $C_{9'}$), 144.98 ($C_{4'}$ and $C_{6'}$), 20.21 ($C_e$), 21.93 ($C_c$ and $C_d$), 22.50 ($C_1$), 41.05 ($C_a$ and $C_b$), 53.18 ($C_m$), and 54.62 ($C_k$); EIMS (m/z) 308 (M+).

EXAMPLE 6

10-(3'-β-hydroxyethylpiperazinopropyl) phenoxazine. The procedure used for Example 2 was repeated with 1 g (4.31 mmol) of the product of Example 1, 1.5 g KI, 2.12 g $K_2CO_3$ and 2 g (15.4 mmol 19 mL) of β-hydroxyethylpiperazine. The free base was recrystallized in petroleum ether-ether mixture (7:3 by volume) to give 1.16 g of the title compound. UV-$\lambda_{max}$ (MeOH) 217, 239 and 322 nm; IR (KBr) 3060, 2820, 1630, 1595, 1495, 1385, 1270, 1160, 1070, 980, 850, 810 and 735 cm$^{-1}$; $^1$H-NMR ('δ') 6.46-6.76 (m, 8H, ArH, $H_1$-$H_4$ and $H_6$-$H_9$), 1.74 (m, 2H, $H_1$), 2.33-2.80 (M, 12H, $H_a$ and $H_b$, $H_c$ and $H_d$, $H_e$ and $H_m$), 2.79 (s, 1H, Hg, disappearing on $D_2O$ exchange), 3.47-3.65 (m, 4H, $H_k$ and $H_j$); $^{13}$C-NMR 111.34 ($C_1$ and $C_9$), 115.24 ($C_4$ and $C_6$), 120.66 ($C_3$ and $C_7$), 123.50 ($C_2$ and $C_8$), 133.30 ($C_{1'}$ and $C_{9'}$), 144.83 ($C_{4'}$ and $C_{6'}$), 22.58 ($C_1$), 41.72 ($C_m$), 52.96 ($C_a$ and $C_b$), 53.28 ($C_c$ and $C_d$), 55.19 ($C_k$); 57.77 ($C_e$), and 59.34 ($C_f$); MS (m/z) 353 (M+).

EXAMPLE 7

10-(3'-N-pyrrolidinopropyl)phenoxazine. The procedure used for Example 2 was repeated with 1 g of the title product of Example 1, 1.5 g KI, 2 g $K_2CO_3$ and 1.1g (15.5 mmol, 1.3 mL) of pyrrolidine. The product was purified by column chromatography and the oil was converted into the hydrochloride salt (1.02 g). UV-$\lambda_{max}$ (MEOW) 217,239, and 319 nm; IR (KBr) 3300, 2660, 1590, 1490, 1375, 1270, 1130, 920, 820 and 745 cm$^{-1}$; $^1$H-NMR ('δ') 6.46-6.77 (m, 8H, ArH, $H_1$-$H_4$ and $H_6$-$H_9$), 2.01-2.17 (t, 4H, $H_c$ and $H_d$, J=13 Hz), 2.21 (m, 2H, $H_1$), 3.06-3.14 (t, 4H, $H_a$ and $H_b$), and 3.60-3.67 (m, 4H, $H_k$ and $H_m$); $^{13}$C-NMR 111.60 ($C_1$ and $C_9$), 115.66 ($C_4$ and $C_6$), 121.40 ($C_3$ and $C_7$), 123.85 ($C_2$ and $C_8$), 132.73 ($C_{1'}$ and $C_{9'}$), 144.98 ($C_{4'}$ and $C_{6'}$), 22.25 ($C_c$ and $C_d$), 23.30 ($C_1$), 40.90 ($C_a$ and $C_b$), 52.80 ($C_m$), and 53.63 ($C_k$); MS (m/z) 294 (M+).

EXAMPLE 8

10-(4'-chlorobutyl)phenoxazine, (8.4 g) in the pure form was prepared following the procedure used for Example 1 with 7 g phenoxazine, 1.63 g sodium amide and 4.36 mL of 1-bromo-4-chlorobutane (0.038 mol) to produce the title compound. UV-$\lambda_{max}$ (MeOH) 200, 212, 238, and 320 nm; IR (KBr) 3060, 2980, 1630, 1590, 1495, 1380, 1280, 1130, 915, 840 and 730 cm$^{-1}$; $^1$H-NMR ('δ') 6.36-6.74 (m, 8H, ArH, $H_1$-$H_4$ and $H_6$-$H_9$), 1.75 (broad, 4H, $H_1$ and $H_m$), and 3.38-3.50 (m, 4H, $H_k$ and $H_n$), $^{13}$C-NMR 111.43 ($C_1$ and $C_9$), 115.53 ($C_4$ and $C_6$), 121.01 ($C_3$ and $C_7$), 123.83 ($C_2$ and $C_8$), 133.27 ($C_{1'}$ and $C_{9'}$), 145.10 ($C_{4'}$ and $C_{6'}$), 22.60 ($C_m$), 29.87 ($C_1$), 43.27 ($C_k$), and 44.61 ($C_n$); EIMS (m/z) 273 (M+).

EXAMPLE 9

10-(4'-diethylaminobutyl)phenoxazine. The procedure used for Example 2 was followed with 1 g (3.65 mmol) of the product of Example 8, 1.5g KI, 2 g $K_2CO_3$ and 1.07 g (14.63 mmol, 1.5 mL) of N,N-diethylamine to obtain the indicated product. The oily product was chromato-graphed on the silica gel with $CH_3OH$—$CHCl_3$ (3:1) and the hydrochloride salt (0.076 g) was obtained in the pure form. UV-$\lambda_{max}$ (MeOH) 201, 213,239 and 320 nm; IR (KBr) 3300, 2940, 1590, 1495, 1380, 1270, 1130, 1040, 925 and 750 cm$^{-1}$; $^1$H-NMR ('δ') 6.47–6.80 (m, 8H, ArH, $H_1$–$H_4$ and $H_6$–$H_9$), 1.33 (broad, 6H, $H_c$ and $H_d$), 1.66–1.91 (m, 4H, $H_1$ and $H_m$), 3.05 (very broad, 6H, $H_a$, $H_b$ and $H_n$), and 3.50 (m, 2H, $H_k$); $^{13}$C-NMR 111.51 ($C_1$ and $C_9$), 115.31 ($C_4$ and $C_6$), 120.99 ($C_3$ and $C_7$), 123.75 ($C_2$ and $C_8$), 132.78 ($C_{1'}$ and $C_{9'}$), 144.78 ($C_{4'}$ and $C_{6'}$), 8.54 ($C_c$ and $C_d$), 21.02 ($C_m$), 22.46 ($C_1$), 43.05 ($C_a$ and $C_b$), 46.50 ($C_n$), and 51.26 ($C_k$); MS (m/z) 310 (M+).

EXAMPLE 10

10-(4'-bishydroxyethylaminobutyl) phenoxazine, as its hydrochloride salt (1.11 g) was obtained by following the procedure of Example 3 with 1 g of the product of Example 8, 1.5 g KI and 1.54 g (14.65 mmol, 1.4 mL) of N,N-diethanolamine followed by column chromatography. UV-$\lambda_{max}$ (MeOH) 204, 210, 238 and 321 nm; IR (KBr) 3280, 2850, 1630, 1590, 1490, 1375, 1270, 1135, 1095, 1065, 1045, 1020, 925, 890, 845, and 740 cm$^{-1}$; $^1$H-NMR ('δ') 6.52–6.84 (m, 8H, ArH, $H_1$–$H_4$ and $H_6$–$H_9$), 1.70–1.98 (m, 4H, $H_1$, and $H_m$), 3.35–3.57 (broad, 10H, $H_a$, $H_b$, $H_n$, $H_k$, $H_e$ and $H_f$), 3.95 (t, 4H, $H_c$ and $H_d$; J=7 Hz), and 10.3 (H+); $^{13}$C-NMR 110.53 ($C_1$ and $C_9$), 114.17 ($C_4$ and $C_6$), 119.83 ($C_3$ and $C_7$), 122.76 ($C_2$ and $C_8$), 131.85 ($C_{1'}$ and $C_{9'}$), 143.60 ($C_{4'}$ and $C_{6'}$), 19.98 ($C_m$), 21.10 ($C_1$), 42.06 ($C_n$), 52.92 ($C_a$ and $C_b$), 54.78 ($C_k$), and 54.96 ($C_c$ and $C_d$); EIMS (m/z) 342 (M+).

EXAMPLE 11

10-(4'-N-morpholinobutyl)phenoxazine. The procedure used for Example 4 was repeated with 1 g of the product of Example 8, 1.5 g KI, 2 g of $K_2CO_3$ and 1.273 g (14.61 mmol, 1.3 mL) of morpholine. The product was recrystallized in ether-petroleum ether mixture (3:1) to give the title compound (0.95 g). UV-$\lambda$-$_{max}$ 202, 213, 239, and 321 nm; IR (KBr) 2960, 2810, 1630, 1595, 1495, 1380, 1295, 1220, 1130, 1070, 1010, 970, 920, 870, 855, 825, 765 and 745 cm$^{-1}$; $^1$H-NMR ('δ') 6.53–7.29 (m, 8H, ArH, $H_1$–$H_4$ and $H_6$–$H_9$), 1.61–1.74 (m, 4H, $H_1$ and $H_m$), 2.40–2.50 (m, 6H, $H_a$, $H_b$, and $H_n$), 3.49 (m, 2H, $H_k$), and 3.49–3.78 (t, 4H, $H_c$ and $H_d$, J=12 Hz); $^{13}$C-NMR 111.28 ($C_1$ and $C_9$), 115.28 ($C_4$ and $C_6$), 120.67 ($C_3$ and $C_7$), 123.52 ($C_2$ and $C_8$), 133.30 ($C_{1'}$ and $C_{9'}$), 144.99 ($C_{4'}$ and $C_{6'}$), 22.34 ($C_m$), 23.50 ($C_1$), 43.63 ($C_n$), 53.67 ($C_a$ and $C_b$), 57.91 ($C_k$), and 66.97 ($C_c$ and $C_d$); EIMS (m/z) 324 (M+).

EXAMPLE 12

10-(4'-N-piperidinobutyl)phenoxazine. 1 g of the product of Example 8, 1.5 g of KI, 2 g $K_2CO_3$ and 1.45 g (17.03 mmol, 1.5 mL) of piperidine were refluxed and processed according to the procedure used for Example 10. Purification by column chromatography afforded the free amine as a brown oil which was converted into the hydrochloride salt (1.18 g). UV-$\lambda_{max}$ 203, 210, 238, and 320 nm; IR (KBr) 3320, 2940, 1625, 1590, 1490, 1380, 1270, 1130, 1060, 955, 840, 820, and 730 cm$^{-1}$; $^1$H-NMR ('δ') 6.42–6.81 (m, 8H, ArH, $H_1$–$H_4$ and $H_6$–$H_9$), 1.44–1.82 (m, 6H, $H_c$, $H_d$ and $H_e$), 1.98–21.8 (m, $H_1$ and $H_m$), 2.70–2.97 (m, 4H, $H_a$ and $H_b$), 3.39–3.45 (m, 4H, $H_k$ and $H_n$) and 11.54 (H+); $^{13}$C-NMR 111.42 ($C_1$ and $C_9$), 115.32 ($C_4$ and $C_6$), 120.98 ($C_3$ and $C_7$), 123.71 ($C_2$ and $C_8$), 132.78 ($C_{1'}$ and $C_{9'}$), 144.73 ($C_{4'}$ and $C_{6'}$), 20.96 ($C_e$), 21.79 ($C_c$ and $C_d$), 22.48 ($C_1$ and $C_m$), 43.08 ($C_a$ and $C_b$), 52.91 ($C_n$), and 56.70 ($C_k$); EIMS (m/z) 322 (M+).

EXAMPLE 13

10-(4'-β-hydroxyethylpiperazinobutyl) phenoxazine. The procedure used for Example 6 was repeated with 1 g of the product of Example 8, 1.5 g KI, and 1.9 g (14.6 mmol, 1.8 mL) of β-hydroxyethylpiperazine. The oily residue was treated with 500 µl of ethylacetate first and then with petroleum ether (20 mL), when a white crystalline solid separated out. The solid was recrystallized to give the pure title compound (1.21 g). UV-$\lambda_{max}$ (MeOH) 202, 239, and 320 nm; IR (KBr) 3060, 2940, 2860, 1590, 1495, 1380, 1225, 1135, 1020, 1005, 935, 880, 830, 780, and 740 cm$^{-1}$; $^1$H-NMR ('δ') 6.46–6.75 (m, 8H, ArH, $H_1$–$H_4$ and $H_6$ and $H_9$), 1.58 (broad, 4H, $H_1$ and $H_m$), 2.36–2.51 (m, 12H, $H_a$, $H_b$, $H_c$, $H_d$, $H_e$ and $H_n$), 3.42 (broad, 3H, $H_k$, and $H_g$), and 3.58–3.63 (t, 2H, $H_f$; J=7 Hz); $^{13}$C-NMR 111.39 ($C_1$ and $C_9$), 115.26 ($C_4$ and $C_6$), 120.64 ($C_3$ and $C_7$), 123.61 ($C_2$ and $C_8$), 133.30 ($C_{1'}$ and $C_{9'}$), 144.95 ($C_{4'}$ and $C_{6'}$), 22.28 ($C_1$ and $C_m$), 23.72 ($C_n$), 43.60 ($C_a$ and $C_b$), 53.11 ($C_c$ and $C_d$), 57.38 ($C_k$), 57.96 ($C_e$) and 59.76 ($C_f$); EIMS (m/z) 367 (M+).

EXAMPLE 14

10-(4'-N-pyrrolidinobutyl)phenoxazine. The experimental steps used for Example 2 were repeated using 1 g of the product of Example 8, 1.5 g KI, 2 g $K_2CO_3$ and 1.04 g (14.6 mmol, 1.22 mL) of pyrrolidine as reactants. The product was chromatographed on silica gel with $CHCl_3$—MeOH (1:1) to give the free amine as a brown oil. An ether solution of this oil was treated with ethereal hydrogen chloride to secure the pure (0.9 g) hydrochloride salt. UV-$\lambda_{max}$ (MeOH) 205, 211, 238 and 320 nm; IR (KBr) 3060, 2840, 1590, 1495, 1380, 1295, 1270, 1160, 1090, 1045, 915, 840, 830, 795, and 740 cm$^{-1}$; $^1$H-NMR ('δ') 6.43–6.79 (m, 8H, ArH, $H_1$–$H_4$ and $H_6$–$H_9$), 1.64–2.10 (m, 8H, $H_1$, $H_m$, $H_c$ and $H_d$), 2.97–3.17 (m, 6H, $H_a$, $H_b$ and $H_n$), 3.45–3.54 (m, 2H, $H_k$) and 10.10 (H+); $^{13}$C-NMR 111.43 ($C_1$ and $C_9$), 115.41 ($C_4$ and $C_6$), 121.01 ($C_3$ and $C_7$), 123.73 ($C_2$ and $C_8$), 132.89 ($C_{1'}$ and $C_{9'}$), 144.87 ($C_{4'}$ and $C_{6'}$), 22.47 ($C_c$ and $C_d$), 23.27 ($C_1$ and $C_m$), 43.14 ($C_a$ and $C_b$), 53.50 ($C_n$), and 54.91 ($C_k$); EIMS (m/z) 308 ((M+).

EXAMPLE 15

10-(chloroacetyl)phenoxazine. To a solution of 5 g (0.03 mol) of phenoxazine dissolved in 100 mL anhydrous acetonitrile containing 10 mL of anhydrous ether, was added dropwise 7 mL (9.926 g, 0,088 mol) of chloroacetyl-chloride with constant stirring. The reaction mixture was stirred at room temperature for 5 H when white crystalline solid separated out (TLC, system A, $R_f$=0.030). The crystals were filtered, washed several times with petroleum ether-ether mixture (9:1) and dried under high vacuum to get 6.03 g of the product. UV-$\lambda_{max}$ (MeOH) 218, 249, and 287 nm; IR (KBr) 3070, 1675, 1580, 1480, 1410, 1350, 1260, 1210, 1115, 1040, 860, 815, 750 and 660 cm$^{-1}$; $^1$H-NMR ('δ') 7.55–7.61 (m, 2H, ArH, $H_1$ and $H_9$), 7.12–7.25 (m, 6H, ArH, $H_2$–$H_4$ and $H_6$–$H_8$), 4.32 (s, 2H, $H_1$); $^{13}$C-NMR 110.04 ($C_1$ and $C_9$), 117.11 ($C_4$ and $C_6$), 123.75 ($C_3$ and $C_7$), 124.32 ($C_2$ and $C_8$), 127.60 ($C_{1'}$ and $C_{9'}$), 150.95 ($C_{4'}$ and $C_{6'}$), 41.51 ($C_1$), and 170 ($C_k$); EIMS (m/z) 259 (M+).

EXAMPLE 16

10-(diethylaminoacetyl)phenoxazine. 1 g (3.9 mmol) of the product of Example 15 was dissolved in 150 mL of anhydrous acetonitrile and 1.5 g of KI and 1.13 g (15.45 mmol, 1.6 mL) of N,N-diethylamine were added to it. The reaction mixture was refluxed for 1 h when substantial amount of the product was formed (TLC, system B, $R_f=0.40$). The mixture was processed as in Example 2 to get a white crystalline solid which was further recrystallized in ethylacetate and petroleum ether mixture to get the pure compound (0.86 g). UV-$\lambda_{max}$ (MeOH) 220, 246, and 287 nm; IR (KBr) 2800, 1685, 1580, 1480, 1320, 1210, 1150, 1060, 1035, 940, 860, 810, 755 and 670 cm$^{-1}$; $^1$H-NMR ('$\delta$') 7.53-7.59 (m, 2H, ArH, $H_1$ and $H_9$), 7.05-7.20 (m, 6H, ArH, $H_2$-$H_4$ and $H_6$-$H_8$), 0.95 (t, 6H, $H_c$ and $H_d$, J=7 Hz), 2.60 (q, 4H, $H_a$ and $H_b$), and 3.55 (s, 2H, $H_1$); $^{13}$C-NMR 116.79 ($C_1$ and $C_9$), 123.31 ($C_4$ and $C_6$), 125.02 ($C_3$ and $C_7$), 126.82 ($C_2$ and $C_8$), 129.62 ($C_{1'}$ and $C_{9'}$), 151.07 ($C_{4'}$ and $C_{6'}$), 12.08 ($C_c$ and $C_d$), 47.04 ($C_a$ and $C_b$), 54.99 ($C_1$), and 169.84 ($C_k$); MS (m/z) 296 ((M+).

EXAMPLE 17

10-(N-morpholinoacetyl)phenoxazine. The same procedure used for Example 16 was employed with 1 g of the product of Example 15, 1.5 g KI and 1.347 g (16 mmol, 1.4 mL) of morpholine. The solid product was recrystallized in a mixture of ethylacetate, petroleum ether and ether and the free base was converted into hydrochloride salt (1.07 g) using ethereal hydrochloride. UV-$\lambda_{max}$ 213, 246, and 287 nm; IR (KBr) 2980, 2860, 1690, 1485, 1440, 1355, 1270, 1180, 1120, 1070, 1005, 900, 870, 855, 760 and 640 cm$^{-1}$; $^1$H-NMR ('$\delta$') 7.60 (broad, 2H, ArH, $H_1$ and $H_9$), 7.12-7.34 (m, 6H, ArH, $H_2$-$H_4$ and $H_6$-$H_8$), 2.40-2.60 (t, 64, $H_a$ and $H_b$, J=12 Hz), 3.35 (s, 2H, $H_1$) and 3.50-3.70 (t, 4H, $H_c$ and $H_d$); $^{13}$C-NMR 117.03 ($C_1$ and $C_9$), 123.90 ($C_4$ and $C_6$), 124.98 ($C_3$ and $C_7$), 126.95 ($C_2$ and $C_8$), 127.91 ($C_{1'}$ and $C_{9'}$), 150.54 ($C_{4'}$ and $C_{6'}$), 52.41 ($C_a$ and $C_b$), 57.01 ($C_1$), 63.23 ($C_c$ and $C_d$), and 163.40 ($C_k$); MS (m/z) 310 ((M+).

EXAMPLE 18

10-(N-piperidinoacetyl)phenoxazine. The method employed for Example 17 was used with 1 g of the product of Example 15, 1.5 g KI and 1.31 g (15.4 mmol, 1.52 mL) of piperidine to get 0.95 g of the title compound. UV-$\lambda_{max}$ (MeOH) 218, 246 and 287 nm; IR (KBr) 2960, 1670, 1610, 1580, 1480, 1370, 1330, 1260, 1190, 1120, 1040, 940, 890, 855, 810, 765, and 655 cm$^{-1}$; $^1$H-NMR ('$\delta$') 7.57-7.61 (m, 2H, ArH, $H_1$ and $H_9$), 7.12-7.16 (m, 6H, ArH, $H_2$-$H_4$ and $H_6$-$H_8$), 1.51 (very broad, 6H, $H_c$, $H_d$ and $H_e$), 2.44 (m, 4H, $H_a$ and $H_b$) and 3.34 (s, 2H, $H_1$); $^{13}$C-NMR 116.72 ($C_1$ and $C_9$), 123.28 ($C_4$ and $C_6$), 124.97 ($C_3$ and $C_7$), 126.79 ($C_2$ and $C_8$), 129.48 ($C_{1'}$ and $C_{9'}$), 151.01 ($C_{4'}$ and $C_{6'}$), 23.92 ($C_e$), 25.93 ($C_c$ and $C_d$), 54.15 ($C_a$ and $C_b$), 60.80 ($C_1$), and 168.92 ($C_k$); EIMS (m/z) 308 (M+).

EXAMPLE 19

10-($\beta$-hydroxyethylpiperazinoacetyl)phenoxazine. The procedure used for Example 17 was repeated with 1 g of the product of Example 15, 1.5 g KI and 2 g (15.4 mmol, 1.9 mL) of $\beta$-hydroxyethylpiperazine Recrystallization of the white solid yielded 1.17 g of the title compound. UV$_{max}$ (MeOH) 213, 246 and 287 nm; IR (KBr) 3200, 2940, 1.685, 1665, 1480, 1265, 1190, 1160, 945, 855, 765 and 640 cm$^{-1}$; $^1$H-NMR ('$\delta$') 7.53-7.58 (m, 2H, ArH, $H_1$ and $H_9$), 7.08-7.25 (m, 6H, ArH, $H_2$-$H_4$ and $H_6$-$H_8$), 2.48 (m, 10H, $H_a$, $H_b$, $H_c$, $H_d$ and $H_e$), 2.70 (s, 1H, $H_g$, disappearing on $D_2O$ exchange), 3.39 (s, 2H, $H_1$) and 3.60 (t, 2H, $H_f$, J=7 Hz); $^{13}$C-NMR 116.85 ($C_1$ and $C_9$), 123.34 ($C_4$ and $C_6$), 124.86 ($C_3$ and $C_7$), 126.99 ($C_2$ and $C_8$), 129.25 ($C_{1'}$ and $C_{9'}$), 151.04 ($C_{4'}$ and $C_{6'}$), 52.70 ($C_a$ and $C_b$), 52.90 ($C_c$ and $C_d$), 57.70 ($C_g$), 59.23 ($C_1$), 59.80 ($C_f$), and 168.43 ($C_k$); EIMS (m/z) 353 (M+).

EXAMPLE 20

10-(N-pyrrolidinoacetyl)phenoxazine. The experimental procedure used for Example 17 was employed with 1 g of the product of Example 15, 1.5 g KI and 1.095 g (15.4 mmol, 1.3 mL) of pyrrolidine. Purification by recrystallization afforded 1.02 g of the title compound. UV-$\lambda_{max}$ (MeOH) 214, 240, and 286 nm; IR (KBr) 2980, 2820, 1695, 1670, 1480, 1455, 1340, 1270, 1180, 1100, 1040, 985, 905, 855, 755 and 640 cm$^{-1}$; $^1$H-NMR ('$\delta$') 7.58-7.63 (m, 2H, ArH, $H_1$ and $H_9$), 7.07-7.18 (m, 6H, ArH, $H_2$-$H_4$ and $H_6$-$H_8$), 1.77 (t, 4H, $H_c$ and $H_d$, J=7 Hz), 2.64 (t, 4H, $H_a$ and $H_b$) and 3.51 (s, 2H, $H_1$); $^{13}$C-NMR 116.80 ($C_1$ and $C_9$), 123.33 ($C_4$ and $C_6$), 125.06 ($C_3$ and $C_7$), 126.85 ($C_2$ and $C_8$), 129.28 ($C_{1'}$ and $C_{9'}$), 151.00 ($C_{4'}$ and $C_{6'}$), 23.73 ($C_c$ and $C_d$), 53.83 ($C_a$ and $C_b$), 57.24 ($C_1$), and 168.92 ($C_k$); EIMS (m/z) 294 (M+).

EXAMPLE 21

10-(trifluoroacetyl)phenoxazine. To a solution of 200 mg of phenoxazine in 10 mL anhydrous chloroform and 4 mL anhydrous ether, was added 50 $\mu$l of (0.7435 g, 3.54 mmol) trifluoroacetic anhydride. The resulting mixture was stirred at room temperature for 8 hours. The formation of the product was monitored by TLC (system A). The product solution was then extracted with chloroform and evaporated. The residue was subjected to column chromatography which afforded the pure title compound. UV-$\lambda_{max}$ (MeOH) 212, 238, and 252 nm; IR (KBr) 3375, 1695, 1580, 1480, 1455, 1390, 1290, 1170, 1110, 1030, 965, 890, 850, 800, 760, 730, and 670 cm$^{-1}$; $^1$H-NMR ('$\delta$') 7.57-7.61 (m, 2H, ArH, $H_1$ and $H_9$), 7.14-7.32 (m, 6H, ArH, $H_2$-$H_4$ and $H_6$-$H_8$); $^{13}$-C-NMR 117.20 ($C_1$ and $C_9$), 123.83 ($C_4$ and $C_6$), 124.34 ($C_3$ and $C_7$), 128.34 ($C_2$ and $C_8$), 151.04 ($C_{1'}$ and $C_{9'}$, and $C_{4'}$ and $C_{6'}$), and >200 ppm ($C_k$ and $C_1$); EIMS (m/z) 279 (M+).

TABLE I

PHYSICAL PROPERTIES OF N-(ALKYLAMINO) OR N-ACYLAMINO DERIVATIVES OF PHENOXAZINE

| Product Of Example No. | Yeild, % | mp, °C. |
| --- | --- | --- |
| 1 | 80 | 53 |
| 2 | 70 | ND |
| 3 | 90 | 83–84 |
| 4 | 80 | 198* |
| 5 | 70 | 202* |
| 6 | 85 | 108 |
| 7 | 75 | 158–159* |
| 8 | 80 | 46 |
| 9 | 60 | 127* |
| 10 | 80 | 115* |
| 11 | 80 | 89 |
|  |  | 187* |
| 12 | 90 | 190* |
| 13 | 90 | 114 |
| 14 | 70 | 170* |
| 15 | 85 | 143–144 |
| 16 | 75 | 39 |
| 17 | 80 | 130* |

TABLE I-continued
PHYSICAL PROPERTIES OF N-(ALKYLAMINO) OR N-ACYLAMINO DERIVATIVES OF PHENOXAZINE

| Product Of Example No. | Yeild, % | mp, °C. |
|---|---|---|
| 18 | 80 | 110–111 |
| 19 | 85 | 70–71 |
| 20 | 80 | 96–98* |
| 21 | 70 | 90 |

\* - HCl salt

The potentiating agent is preferably administered by infusion in solution in sterile water. The potentiating agents as hydrochloride salts can be dissolved in sterile water. The agents as bases can be solubilized in 1N hydrochloric acid, following which the solution is back titrated with sodium hydroxide to provide a final pH between 7 and 8.

Cytotoxic agents whose cytotoxicity would be potentiated by agents within the scope of this invention include VCR, VLB, doxorubicin, colchicine, actinomycin D, daunomycin, M-AMSA, and other anthracyclic compounds.

The potentiating agent is administered to tumor cells which are exposed to one or more cytotoxic agents. By "exposed" is meant that the cytotoxic agent has been administered simultaneously with the potentiating agent, and/or is administered subsequently to the administration of the potentiating agent, so long as at least some of the cytotoxic agent(s) is present in the tumor cell when the potentiating agent is present in the tumor cell. The cytotoxic agent should not be administered before the potentiating agent. Preferably, the cytotoxic agent is administered when the potentiating agent concentration reaches steady state during administration by infusion.

It will be recognized that the amount of potentiating agent to be administered will vary between hosts, between cytotoxic agents and between potentiating agents, but the effective amounts can readily be ascertained by those of ordinary skill in this field. As guidance one can refer to the data in Examples 22–24 as well as the following Table. In general, though, effective amounts to potentiate cytotoxic agents are about 2000–3000 moles of potentiating agent per mole of VCR; about 1,000–2,000 moles of potentiating agent per mole of VLB; and about 25–35 moles of potentiating agent per mole of VP-16 (Etoposide). These values, and the corresponding values for any other cytotoxic agents, can readily be converted if desired into dosages per host body weight by calculation based on the dosages for the cytotoxic agent of interest. The in vitro techniques described herein can be employed to determine the effectiveness of any particular potentiating agent with any given cytotoxic agent or agents.

EXAMPLE 22

Table II below gives representative in vivo values of the molar ratios (shown below as "compound: (cytotoxic agent)") of potentiating agent to cytotoxic agent for compounds within the scope of this invention. Vincristine (VCR) was administered to mice at 3 mg/kg (3.25 μmol/kg); vinblastine (VLB) was at 5 mg/kg (5.5 μmol/kg); VP-16 (Etoposide) was at 50 mg/kg/day for 3 days (0.255 mmol/kg total). The compound number is the number of the example in which the potentiating agent was prepared.

TABLE II

| Compound No. | Compound: VCR | Compound: VLB | Compound: VP-16 |
|---|---|---|---|
| 3 | 2345 | 1388 | 29.9 |
| 4 | 2483 | 1469 | 31.6 |
| 11 | 2375 | 1405 | 30.3 |
| 18 | 2498 | 1478 | 31.8 |

EXAMPLE 23
Evaluation of N-substituted Phenoxazines for Anti-MDR Activity

A cloned line of human colon adenocarcinoma, $GC_3/Cl^{31}$, which is intrinsically resistant to VCR ($\approx$4-fold relative to KB-3-1), was routinely grown at 37° C. in antibiotic-free RPMI-1640 medium supplemented with 2 mM glutamine and 10% FBS (Hyclone Laboratories, Inc., Logan, Utah) in a humidified atmosphere of 5% $CO_2$ and 95% air. Human epidermoid carcinoma KB-3-1 cells and a colchicine selected MDR variant, KBCh®-8-5, were obtained which was cross-resistant to VCR (45-fold) and VLB (6.3-fold); it was grown in monolayer culture at 37° C. in DMEM with 10% FBS and L-glutamine in a humidified atmosphere of 10% $CO_2$ in air. The resistance of the KBCh®-8-5 cells was maintained by culturing them with colchicine (10 ng/ml).

Then, 2 mL of cell suspensions ($2 \times 10^6$) were plated in 35×10 mm style "easy grip" culture dishes (Becton Dickinson Co., Lincoln Park, N.J.). Cells were allowed to attach to plastic overnight at 37° C. Medium was aspirated and cells were washed with (2×2 mL) physiologic tris (PT) buffer. Monolayers were incubated at room temperature for 10 minutes in PT buffer prior to aspiration and adding 1 mL of serum-free RPMI-1640 Hepes buffer (10.4 g RPMI-1640 medium in IL of 25 mM Hepes, pH 7.4) containing 70.4 nm [$^3$H] VCR (sp.act. 7.1 ci/mmol) or 49.5 nm [$^3$H] VLB (sp. act. 10.1 Ci/mmol) with or without a compound of Examples 1–21 (100 μM) or VRP dissolved in $H_2O$ dissolved in DMSO (final culture concentration <0.1% DMSO). After 2 h of incubation at room temperature, medium was rapidly aspirated to terminate drug accumulation, and monolayers were washed four times with ice-cold PBS (g/L: NaCL 8.0; $Na_2HPO_4.12H_2O$, 2.9; KCl 0.2; $KH_2PO_4$, 0.2) and drained. To each dish, 1 ml of trypsin-EDTA (0.05% trypsin, 0.53 mM EDTA) was added. After 1 minute, monolayers were triturated to give a uniform suspension of cells, and radioactivity in 0.75 ml was determined by scintillation counting. Cell number per dish was determined on 200 μl of suspension using the method of Butler, and amounts of intracellular VCR or VLB were determined. The results are set forth in Table III, in which the compound number is the number of the Example in which the compound (or "modulator" or "potentiating agent") was prepared.

TABLE III
EFFECTS OF N-SUBSTITUTED PHENOXAZINES ON MDR ACTIVITY

| Modulator Compound Number | Vinca Accumulation $^a$(% control) | | | |
|---|---|---|---|---|
| | KB Ch$^R$-8-5 Cells | | $GC_3/Cl$ Cells | |
| | VCR | VLB | VCR | VLB |
| 1 | 454 | 342 | 846 | 570 |
| 2 | 546 | 2123 | 439 | 1025 |
| 3 | 473 | 1666 | 464 | 1070 |
| 4 | 742 | 1717 | 634 | 960 |
| 5 | 435 | 1227 | 282 | 633 |

TABLE III-continued

EFFECTS OF N-SUBSTITUTED PHENOXAZINES ON MDR ACTIVITY

| Modulator Compound Number | Vinca Accumulation $^a$(% control) | | | |
|---|---|---|---|---|
| | KB Ch$^R$-8-5 Cells | | GC$_3$/Cl Cells | |
| | VCR | VLB | VCR | VLB |
| 6 | 343 | 824 | 368 | 879 |
| 7 | 408 | 969 | 250 | 757 |
| 8 | 398 | 792 | 317 | 361 |
| 9 | 211 | 697 | 325 | 737 |
| 10 | 92 | 403 | 382 | 1165 |
| 11 | 702 | 2684 | 477 | 1175 |
| 12 | 196 | 1071 | 416 | 1121 |
| 13 | 91 | 188 | 543 | 1340 |
| 14 | 198 | 477 | 412 | 1315 |
| 15 | 138 | 236 | 171 | 284 |
| 16 | 184 | 953 | 160 | 305 |
| 17 | 290 | 674 | 213 | 298 |
| 18 | 326 | 2023 | 177 | 446 |
| 19 | 280 | 776 | 157 | 426 |
| 20 | 188 | 776 | 151 | 296 |
| 21 | 415 | 827 | 230 | 222 |
| Verapamil | 402 | 1124 | 178 | 238 |

$a \frac{\text{vinca uptake with modulator}}{\text{vinca uptake without modulator}} \times 100$ $^b$Compounds were tested at 100 μM. All values represent the mean of two separate experiments with a SD of less than 10% of the mean; each experiment was done in triplicate.

EXAMPLE 24

Evaluation of N-substituted Phenoxazines Cytotoxicity to Tumor Cells

The KBCh®-8-5 cells were plated in triplicate at a density of 1000 cells per well and GC$_3$ at 3000 cells per well in Falcon 6-well flat-bottom tissue culture plates (Becton Dickinson Co., Lincoln Park, N.J.). After 24 h, incubation medium was replaced with 3 mL of fresh medium containing compounds 1-4 or 10-14 or 18 at concentrations ranging from 1-100 μm (final culture concentration, 0.1% DMSO), and cells were incubated at 37° C. for a further 7 days. The medium was aspirated and cells were washed once with 2 mL of 0.9% saline and dried overnight. Colonies were stained with 1 mL of 0.1% crystal violet followed by washing twice with distilled water and were counted using an automated ARTEK Model 880 colony counter. The IC$_{50}$ values were determined from concentration-percent-cell-survival curves and were defined as the concentrations of phenoxazines required for 50% reduction in colonies compared to controls. The results of these measurements are set forth in Table IV.

TABLE IV

CYTOTOXICITY OF N-SUBSTITUTED PHENOXAZINES

| | IC$_{50}$, $^a$μM | |
|---|---|---|
| Compound Number | KBCh$^R$-8-5 | GC$_3$/CL |
| 1 | 57 | 83.00 |
| 2 | 15 | ND |
| 3 | 38 | 37 |
| 4 | 73 | 40 |
| 10 | <10 | 16 |
| 11 | 18 | 27 |
| 12 | <10 | 7 |
| 13 | <10 | 7 |
| 14 | <10 | 8 |
| 18 | 73 | ND |

$^a$IC$_{50}$ is the concentration required to produce 50% reduction in clonogenic survival of GC$_3$/Cl and KBCH$^R$-8-5 cells under the conditions described in Example 23.

EXAMPLE 25

Effect of N-substituted Phenoxazines on In Vitro Cytotoxicity of VLB and VCR

Tumor cells were treated with graded concentrations of VCR and VLB in the absence or presence of non-toxic concentrations of the products of Examples 1, 3, 4 and 18. The plates were then transferred to a CO$_2$ incubator and, after further incubation for 7 days at 37° C., colonies were enumerated as described in Example 23. The results are set forth in Table V.

TABLE V

Potentiation Of Cytotoxicity Of Vincristine And Vinblastine By N-substituted Phenoxazines Against GC$_3$/Cl And KBCh$^R$-8-5 Cells

| Compound Number | Concentration of Modulator$^a$ (μM) | IC$_{50}$ Values, nM | | | |
|---|---|---|---|---|---|
| | | KB Ch$^R$-8-5 Cells | | GC$_3$/Cl Cells | |
| | | VCR | VLB | VCR | VLB |
| no modulator | — | 32.0 | 20.0 | 27.0 | 7.4 |
| 1 | 50 | — | — | 9.0 | — |
| 3 | 25 | — | 2.7 | — | 2.0 |
| 4 | 25 | 1.2 | 1.6 | 0.85 | 2.0 |
| 18 | 49 | — | 2.3 | — | 2.2 |

$^a$IC$_{50}$ concentration of modulator

What is claimed is:

1. A method of potentiating the cytotoxicity of an agent cytotoxic to a tumor cell, comprising administering to said tumor cell, while it is exposed to said cytotoxic agent, a potentiating agent in an amount effective to potentiate the cytotoxicity of said cytotoxic agent to said cell, wherein said potentiating agent consists of one or more of the compounds of the formula (1):

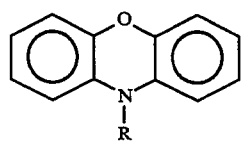

(1)

or a pharmacologically acceptable salt thereof,
  wherein R is —H or —[C(O)]$_a$—(CH$_2$)$_b$—A;
  wherein a is 0 or 1 and b is an integer from 0 to 6, provided that a and b are not both zero; and
  A is selected from the group consisting of —NR$_1$R$_2$ wherein R$_1$ and R$_2$ are independently alkyl having 1 to 4 carbon atoms, and either or both of R$_1$ and R$_2$ are optionally substituted with —OH;

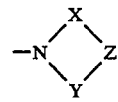

wherein X and Y are independently alkylene having 1 to 4 carbon atoms, and Z is —O—, —N(R$_3$)— or —CH(R$_4$)—, wherein R$_3$ is hydrogen or alkyl having 1 to 4 carbon atoms optionally substituted with a hydroxyl group, and wherein R$_4$ is hydrogen or alkyl having 1 to 4 carbon atoms optionally substituted with a hydroxyl group;
  halide; and trihalomethyl.

2. The method of claim 1 wherein said tumor cell is present in a living host.

3. The method of claim 1 wherein said cytotoxic agent is selected from the group consisting of vincristine, vinblastine, etoposide, doxorubicin, colchicine, actinomycin D, daunomycin, m-AMSA, and mixtures thereof.

4. The method of claim 1 wherein said tumor cell exhibits multiple drug resistance.

5. The method of claim 1 wherein a is zero; b is 3 or 4; $R_1$ and $R_2$ are independently selected from the group consisting of ethyl, propyl, ω-hydroxyethyl, and ω-hydroxypropyl; X and Y are each independently selected from the group consisting of —CH$_2$— and —CH$_2$CH$_2$—; and $R_3$ and $R_4$ are independently selected from the group consisting of —H, ethyl, propyl, ω-hydroxyethyl, and ω-hydroxypropyl.

6. The method of claim 5 wherein said potentiating agent is 10-(3'-chloropropyl)-phenoxazine or a pharmacologically acceptable salt thereof.

7. The method of claim 5 wherein said potentiating agent is 10-(3'-diethylaminopropyl)-phenoxazine or a pharmacologically acceptable salt thereof.

8. The method of claim 5 wherein said potentiating agent is 10-(3'-bishydroxyethylaminopropyl)-phenoxazine or a pharmacologically acceptable salt thereof.

9. The method of claim 5 wherein said potentiating agent is 10-(3'-N-morpholinopropyl)-phenoxazine or a pharmacologically acceptable salt thereof.

10. The method of claim 5 wherein said potentiating agent is 10-(3'-N-piperidinopropyl)-phenoxazine or a pharmacologically acceptable salt thereof.

11. The method of claim 5 wherein said potentiating agent is 10-(3'-β-hydroxyethylpiperazinopropyl)-phenoxazine or a pharmacologically acceptable salt thereof.

12. The method of claim 5 wherein said potentiating agent is 10-(3'-N-pyrrolidinopropyl)-phenoxazine or a pharmacologically acceptable salt thereof.

13. The method of claim 5 wherein said potentiating agent is 10-(4'-chlorobutyl)-phenoxazine or a pharmacologically acceptable salt thereof.

14. The method of claim 5 wherein said potentiating agent is 10-(4'-diethylaminobutyl)-phenoxazine or a pharmacologically acceptable salt thereof.

15. The method of claim 5 wherein said potentiating agent is 10-(4'-bishydroxyethylaminobutyl)-phenoxazine or a pharmacologically acceptable salt thereof.

16. The method of claim 5 wherein said potentiating agent is 10-(4'-N-morpholinobutyl)-phenoxazine or a pharmacologically acceptable salt thereof.

17. The method of claim 5 wherein said potentiating agent is 10-(4'-piperidinobutyl)-phenoxazine or a pharmacologically acceptable salt thereof.

18. The method of claim 5 wherein said potentiating agent is 10-(4'-β-hydroxyethylpiperazinobutyl)-phenoxazine or a pharmacologically acceptable salt thereof.

19. The method of claim 5 wherein said potentiating agent is 10-(4'-N-pyrrolidinobutyl)-phenoxazine or a pharmacologically acceptable salt thereof.

20. The method of claim 1 wherein a is 1.

21. The method of claim 20 wherein b is 1 or 2; $R_1$ and $R_2$ are independently selected from the group consisting of ethyl, propyl, ω-hydroxyethyl, and ω-hydroxypropyl; X and Y are each independently selected from the group consisting of —CH$_2$— and —CH$_2$CH$_2$—; and $R_3$ and $R_4$ are independently selected from the group consisting of —H, ethyl, propyl, ω-hydroxyethyl, and ω-hydroxypropyl.

22. The method of claim 21 wherein said potentiating agent is 10-(chloroacetyl)-phenoxazine or a pharmacologically acceptable salt thereof.

23. The method of claim 21 wherein said potentiating agent is 10-(diethylaminoacetyl)-phenoxazine or a pharmacologically acceptable salt thereof.

24. The method of claim 21 wherein said potentiating agent is 10-(N-morpholinoacetyl)-phenoxazine or a pharmacologically acceptable salt thereof.

25. The method of claim 21 wherein said potentiating agent is 10-(N-piperidinoacetyl)-phenoxazine or a pharmacologically acceptable salt thereof.

26. The method of claim 21 wherein said potentiating agent is 10-(β-hydroxyethylpiperazinoacetyl)-phenoxazine or a pharmacologically acceptable salt thereof.

27. The method of claim 21 wherein said potentiating agent is 10-(N-pyrrolidinoacetyl)-phenoxazine or a pharmacologically acceptable salt thereof.

28. The method of claim 21 wherein said potentiating agent is 10-(trifluoroacetyl)-phenoxazine or a pharmacologically acceptable salt thereof.

29. A composition comprising a cytotoxic agent toxic to tumor cells, and a potentiating agent which potentiates the cytotoxicity of said cytotoxic agent, wherein said potentiating agent consists of one or more of the compound of the formula (1)

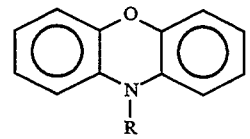

(1)

or a pharmacologically acceptable salt thereof,
wherein R is —H or —[C(O)]$_a$—(CH$_2$)$_b$—A;
wherein a is 0 or 1 and b is an integer from 0 to 6, provided that a and b are not both zero; and
A is selected from the group consisting of —NR$_1$R$_2$ wherein R$_1$ and R$_2$ are independently alkyl having 1 to 4 carbon atoms, and either or both of R$_1$ and R$_2$ are optionally substituted with —OH;

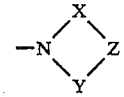

where X and Y are independently alkylene having 1 to 4 carbon atoms, and Z is —O—, —N(R$_3$)— or —CH(R$_4$)—, wherein R$_3$ is hydrogen or alkyl having 1 to 4 carbon atoms optionally substituted with a hydroxyl group, and wherein R$_4$ is hydrogen or alkyl having 1 to 4 carbon atoms optionally substituted with a hydroxyl group;
halide; and trihalomethyl;
provided that when a is one and b is one, A is not halide;
wherein said cytotoxic agent and potentiating agent are present in amounts effective to render the composition cytotoxic to tumor cells.

30. The composition of claim 29 wherein said cytotoxic agent is selected from the group consisting of vincristine, vinblastine, etoposide, doxorubicin, colchicine, actinomycin D, daunomycin, m-AMSA, and mixtures thereof.

31. The composition of claim 29 wherein a is zero; b is 3 or 4; $R_1$ and $R_2$ are independently selected from the group consisting of ethyl, propyl, ω-hydroxyethyl, and ω-hydroxypropyl; X and Y are each independently selected from the group consisting of —CH$_2$— and —CH$_2$CH$_2$—; and R$_3$ and R$_4$ are independently selected from the group consisting of —H, ethyl, propyl, ω-hydroxyethyl, and ω-hydroxypropyl.

32. The composition of claim 31 wherein said potentiating agent is 10-(3'-chloropropyl)-phenoxazine or a pharmacologically acceptable salt thereof.

33. The composition of claim 31 wherein said potentiating agent is 10-(3'-diethylaminopropyl)-phenoxazine or a pharmacologically acceptable salt thereof.

34. The composition of claim 31 wherein said potentiating agent is 10-(3'-bishydroxyethylaminopropyl)-phenoxazine or a pharmacologically acceptable salt thereof.

35. The composition of claim 31 wherein said potentiating agent is 10-(3'-N-morpholinopropyl)-phenoxazine or a pharmacologically acceptable salt thereof.

36. The composition of claim 31 wherein said potentiating agent is 10-(3'-N-piperidinopropyl)-phenoxazine or a pharmacologically acceptable salt thereof.

37. The composition of claim 31 wherein said potentiating agent is 10-(3'-β-hydroxyethylpiperazinopropyl)-phenoxazine or a pharmacologically acceptable salt thereof.

38. The composition of claim 31 wherein said potentiating agent is (10-(3'-N-pyrrolidinopropyl)phenoxazine or a pharmacologically acceptable salt thereof.

39. The composition of claim 31 wherein said potentiating agent is 10-(4'-chlorobutyl)-phenoxazine or a pharmacologically acceptable salt thereof.

40. The composition of claim 31 wherein said potentiating agent is 10-(4'-diethylaminobutyl)-phenoxazine or a pharmacologically acceptable salt thereof.

41. The composition of claim 31 wherein said potentiating agent is 10-(4'-bishydroxyethylaminobutyl)-phenoxazine or a pharmacologically acceptable salt thereof.

42. The composition of claim 31 wherein said potentiating agent is 10-(4'-N-morpholinobutyl)-phenoxazine or a pharmacologically acceptable salt thereof.

43. The composition of claim 31 wherein said potentiating agent is 10-(4'-piperidinobutyl)-phenoxazine or a pharmacologically acceptable salt thereof.

44. The composition of claim 31 wherein said potentiating agent is 10-(4'-β-hydroxyethylpiperazinobutyl)-phenoxazine or a pharmacologically acceptable salt thereof.

45. The composition of claim 31 wherein said potentiating agent is 10-(4'-N-pyrrolidinobutyl)-phenoxazine or a pharmacologically acceptable salt thereof.

46. The composition of claim 29 wherein a is 1; b is 1 or 2; R$_1$ and R$_2$ are independently selected from the group consisting of ethyl, propyl, ω-hydroxyethyl, and ω-hydroxypropyl; wherein X and Y are each independently selected from the group consisting of —CH$_2$— and —CH$_2$CH$_2$—; and R$_3$ and R$_4$ are independently selected from the group consisting of —H, ethyl, propyl, ω-hydroxyethyl, and ω-hydroxypropyl.

47. The composition of claim 46 wherein said potentiating agent is 10-(diethylaminoacetyl)-phenoxazine or a pharmacologically acceptable salt thereof.

48. The composition of claim 46 wherein said potentiating agent is 10-(N-morpholinoacetyl)-phenoxazine or a pharmacologically acceptable salt thereof.

49. The composition of claim 46 wherein said potentiating agent is 10-(N-piperidinoacetyl)-phenoxazine or a pharmacologically acceptable salt thereof.

50. The composition of claim 46 wherein said potentiating agent is 10-(β-hydroxyethylpiperazinoacetyl)-phenoxazine or a pharmacologically acceptable salt thereof.

51. The composition of claim 46 wherein said potentiating agent is 10-(N-pyrrolidinoacetyl)-phenoxazine or a pharmacologically acceptable salt thereof.

52. The composition of claim 46 wherein said potentiating agent is 10-(trifluoroacetyl)-phenoxazine or a pharmacologically acceptable salt thereof.

53. A method of killing a tumor cell which comprises administering to said cell a composition according to claim 29 in an amount effective to kill said cell.

54. The method of claim 53 wherein said tumor cell is present in a living host.

55. The method of claim 53 wherein said tumor cell exhibits multiple drug resistance.

56. A compound selected from the group consisting of 10-(3'-bishydroxyethylaminopropyl)-phenoxazine, 10-(4'-chlorobutyl)-phenoxazine, 10-(4'-bishydroxyethylaminobutyl)-phenoxazine, 10-(4'-β-hydroxyethylpiperazinobutyl)-phenoxazine, 10-(β-hydroxyethylpiperazinoacetyl)-phenoxazine, 10-(trifluoroacetyl)-phenoxazine, and pharmacologically acceptable salts thereof.

57. The compound according to claim 56 which is 10-(3'-bishydroxyethylaminopropyl)-phenoxazine or a pharmacologically acceptable salt thereof.

58. The compound according to claim 56 which is 10-(4'-chlorobutyl)-phenoxazine or a pharmacologically acceptable salt thereof.

59. The compound according to claim 56 which is 10-(4'-bishydroxyethylaminobutyl)-phenoxazine or a pharmacologically acceptable salt thereof.

60. The compound according to claim 56 which is 10-(4'-β-hydroxyethylpiperazinobutyl)-phenoxazine or a pharmacologically acceptable salt thereof.

61. The compound according to claim 56 which is 10-(β-hydroxyethylpiperazinoacetyl)-phenoxazine or a pharmacologically acceptable salt thereof.

62. The compound according to claim 56 which is 10-(trifluoroacetyl)-phenoxazine or a pharmacologically acceptable salt thereof.

* * * * *